(12) United States Patent
Birdwell

(10) Patent No.: US 7,341,376 B2
(45) Date of Patent: Mar. 11, 2008

(54) METHOD FOR ALIGNING RADIOGRAPHIC INSPECTION SYSTEM

(75) Inventor: Thomas William Birdwell, Middletown, OH (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 11/277,269

(22) Filed: Mar. 23, 2006

(65) Prior Publication Data

US 2007/0223657 A1   Sep. 27, 2007

(51) Int. Cl.
*A61B 6/08* (2006.01)

(52) U.S. Cl. ....................... 378/205; 378/203

(58) Field of Classification Search ................ 378/205, 378/207, 117, 57, 203
See application file for complete search history.

(56) References Cited

U.S. PATENT DOCUMENTS

| | | | |
|---|---|---|---|
| 4,296,329 A | 10/1981 | Mirabella | |
| 4,578,806 A | 3/1986 | Grass et al. | |
| 4,809,314 A | 2/1989 | Steele et al. | |
| 6,056,437 A | 5/2000 | Toth | |
| 6,422,750 B1 | 7/2002 | Kwasnick et al. | |
| 6,466,643 B1 | 10/2002 | Bueno et al. | |
| 6,925,140 B2 * | 8/2005 | Bruder | 378/4 |
| 6,935,779 B2 | 8/2005 | Zhang et al. | |
| 6,954,515 B2 | 10/2005 | Bjorkholm et al. | |
| 6,960,020 B2 | 11/2005 | Lai | |
| 6,968,034 B2 | 11/2005 | Ellengogen | |
| 7,020,242 B2 | 3/2006 | Ellenbogen | |
| 7,073,939 B2 | 7/2006 | Spahn | |
| 7,101,078 B1 | 9/2006 | Toth | |
| 2003/0091157 A1 * | 5/2003 | Nakanishi et al. | 378/205 |
| 2004/0037389 A1 * | 2/2004 | De Smet | 378/57 |

* cited by examiner

*Primary Examiner*—Hoon Song
(74) *Attorney, Agent, or Firm*—Adams Intellectual Property Law, PA; William Scott Andes

(57) ABSTRACT

A method for aligning a radiographic inspection system includes providing a radiation source capable of emitting a beam pattern, positioning a detector to receive radiation emitted from the radiation source, and causing the radiation source to emit the beam pattern. The detector is used to determine the distribution of flux intensity of the beam pattern. A two-dimensional or three-dimensional map of the beam pattern may be stored. The system is aligned by positioning the radiation source and the detector with reference to the map, so that the detector is disposed at a predetermined location within the beam pattern.

21 Claims, 4 Drawing Sheets

METHOD FOR ALIGNING RADIOGRAPHIC INSPECTION SYSTEM

BACKGROUND OF THE INVENTION

This invention relates generally to radiographic inspection system, and more particularly to a method of aligning a radiographic source with a detector.

Radiographic apparatus, particularly X-ray apparatus, is used to measure or inspect an object for the purposes of evaluating its characteristics. Radiation projected by a source is absorbed to varying degrees by the inspected object, depending on its size, mass, and configuration. The photons that continue through the object are counted or measured by a detector, and the pattern of flux variation across the object provides information about it. To obtain an optimum image, the X-Ray source, detector, and inspected object must be aligned. Small improvements in this alignment can often provide significant improvement in image quality.

Because X-Rays are ionizing radiation and dangerous to humans, means are required to prevent or minimize personnel exposure. This is accomplished by designating areas of danger and excluding personnel from them, or by creating X-Ray absorbing structures to contain the X-Rays within a reduced area. In the inspection of smaller objects, the objects themselves can be taken to a location containing a shielded and permanently aligned inspection system. For larger objects, such as aircraft fuselages and gas turbine engine components, however, the X-Ray inspection system must be taken to the object, and there assembled and aligned. Depending on the size and configuration of the object and system, the detector and X-Ray tube may not be within line of sight of each other, or even be seen from a single separate location, making alignment of the source, detector, and shielding difficult Prior art X-ray tubes, detectors, and shielding are typically aligned using expensive fixtures, jigs and external sensors, or by approximation and iteration. Images are taken, evaluated, and the system's alignment changed. For inspection of large objects, this is often difficult, slow, and can result in unnecessary exposure to X-Rays. Additionally, sub-optimal images are produced unless the alignment is proper.

Accordingly, there is a need for a method of aligning a radiographic system where a line-of-sight is not available between the source and the detector

BRIEF SUMMARY OF THE INVENTION

The above-mentioned need is met by the present invention, which according to one aspect provides a method for aligning a radiographic inspection system, includes the steps of: providing a radiation source capable of emitting a beam pattern; positioning a detector to receive radiation emitted from the radiation source; causing the radiation source to emit the beam pattern; using the detector to determine the distribution of flux intensity of the beam pattern; and relatively positioning the radiation source and the detector with reference to the map, so that the detector is disposed at a predetermined location within the beam pattern.

According to another aspect of the invention, a method for aligning a radiographic inspection system includes the steps of: providing a radiation source capable of emitting a beam pattern; positioning a detector at a first position relative to the radiation source, so as to receive radiation emitted from the radiation source; causing the radiation source to emit the beam pattern; creating a first group of records of the flux intensity received by the detector at a plurality of points on the detector; creating a map comprising the records, the map describing the flux intensity at a plurality of positions within the beam pattern; and relatively positioning the radiation source and the detector with reference to the map, so that the detector is disposed at a predetermined location within the beam pattern.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
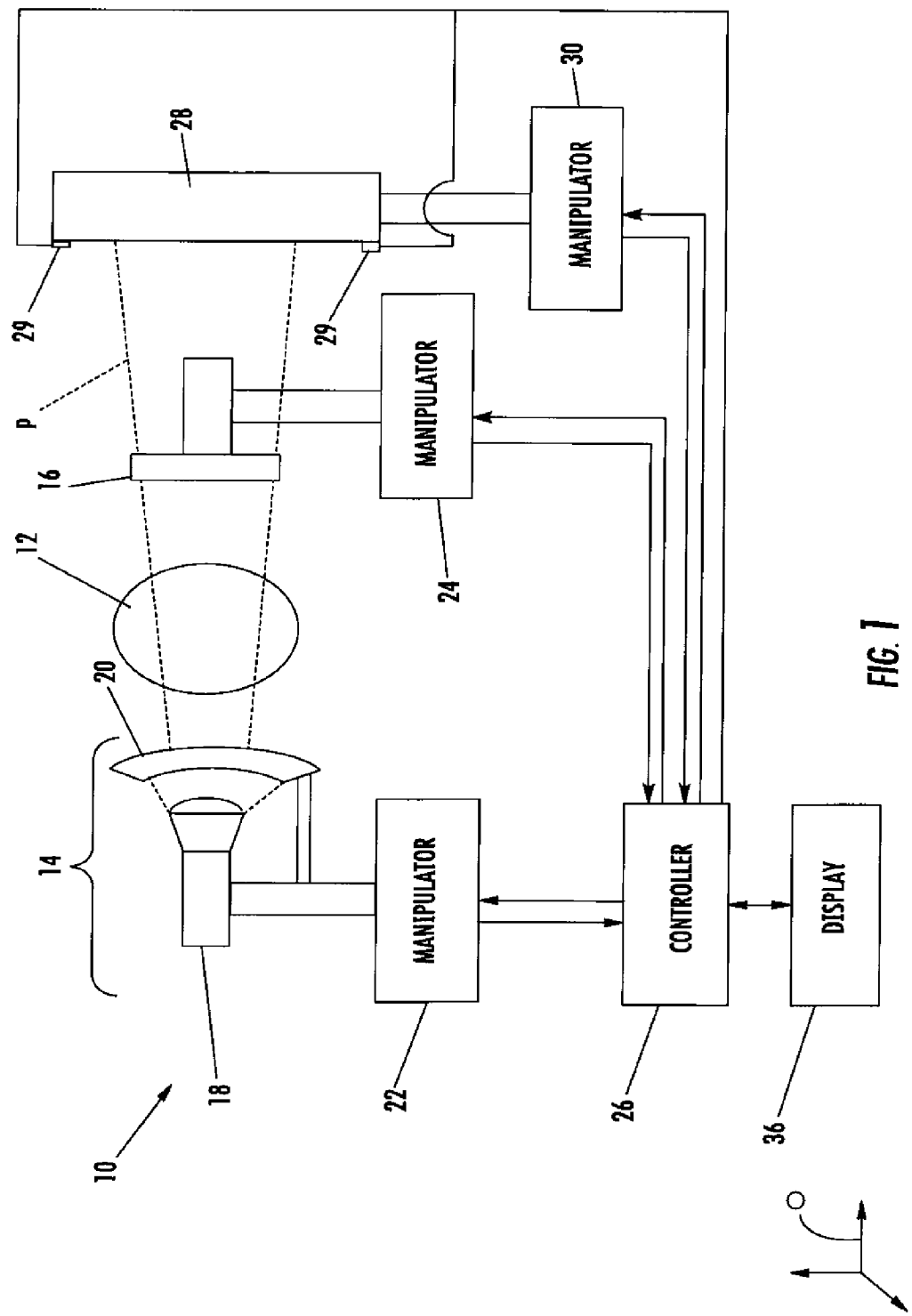
FIG. 1 is a schematic side view of a radiographic inspection system constructed according to the present invention.

Referring to the drawings wherein identical reference numerals denote the same elements throughout the various views, FIG. 1 illustrates schematically a radiographic inspection system 10 disposed around a target 12 to be inspected. The inspection system 10 may be used with various types of structures. The inspection system 10 includes a radiation source 14 located on a first side of the target 12 and a radiation detector 16 located on a second, opposite side of the target 12. The radiation source 14 includes an X-ray tube 18 (an isotopic source could also be used), and may include a collimator 20 of a known type which defines radiation flux generated by the tube 18 into beam. In the illustrated example, the beam (described in more detail below) is cone or fan shaped, but the beam may also be collimated to the shape and size of the detector, or in come cases even collimated in any number of ways to illuminate a particular airframe section and to block out anything around the point of interest and/or to minimize the radiation hazard to nearby personnel. The radiation source 14 and radiation detector 16 are relatively situated so that radiation emitted by the radiation source 14 passes through the target 12 and then impinges on the radiation detector 16. Manipulators 22 and 24 of a known type are provided for the source 14 and detector 16, respectively. The manipulators 22 and 24 are capable of moving the source 14 and the detector 16 to precise positions in three-dimensional space under the direction of an electronic or computerized controller 26, or in response to manual inputs.

Figure 2:
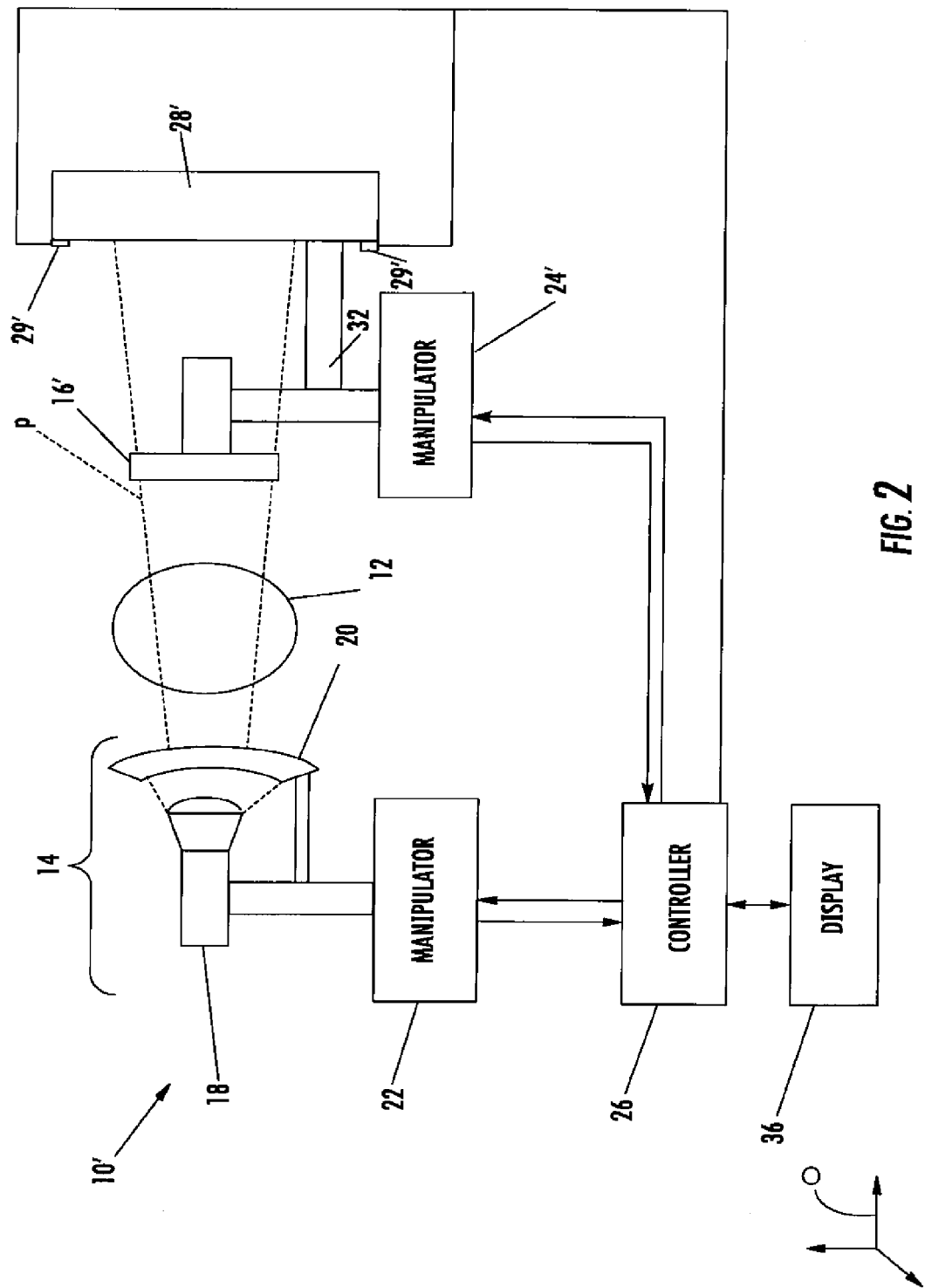
FIG. 2 is a schematic cross-sectional view of an alternative radiographic inspection system.

If the inspection system 10 is to be used where humans are present, shielding may be provided to protect personnel from the ionizing radiation created by the system 10. FIG. 1 depicts a shield 28 constructed of materials which absorb radiation and supported in a position behind the detector 16 by a manipulator 30 of a known type capable of moving the shield 28 to a precise position in three-dimensional space under the direction of the controller 26, or in response to manual inputs. FIG. 2 depicts an alternate inspection system 10' in which a shield 28' is mechanically attached or linked to a detector 16', for example using a bracket 32, so as to be moved in unison therewith by a single manipulator 24'.

Figure 3:
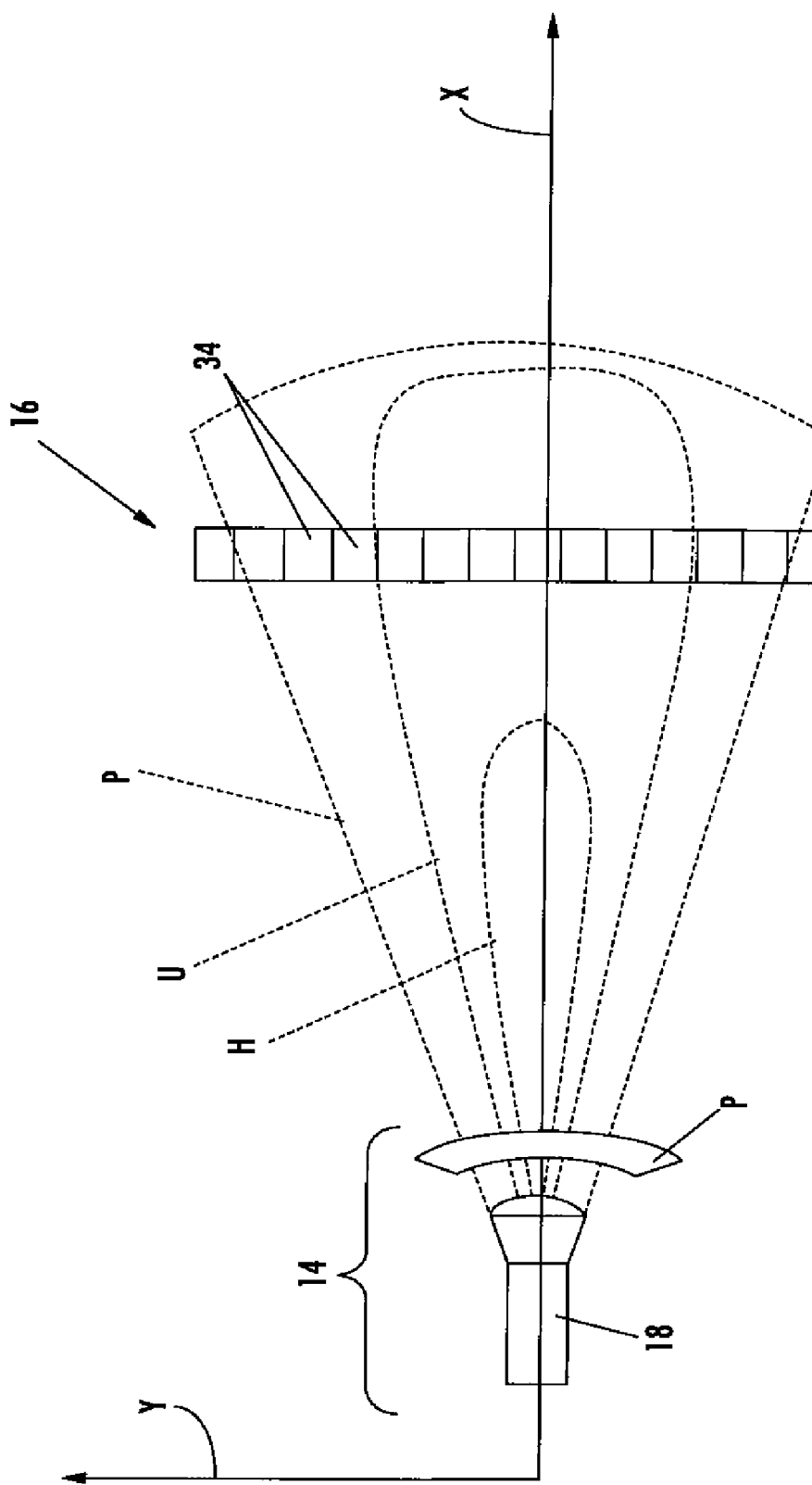
FIG. 3 is a schematic top view of the radiographic inspection system of FIG. 1 undergoing a mapping process.

FIG. 3 illustrates a top-down view of an exemplary beam pattern "P" created by the radiation source 14. This specific example shown is a fan beam pattern P which is collimated into a relatively thin "slice", that is, the beam pattern P has a small thickness in the direction of the paper. The present method could also be applied to a cone beam pattern or other type of pattern (not shown) extending along a longitudinal "X" axis. As seen in FIG. 3, the beam pattern P has lateral boundaries which are defined by the collimator 20. The beam pattern P is affected by the internal geometry of the tube 18, target features, the collimator 20, and other factors. However, each radiation source 14 will generally have a consistent and measurable beam pattern P.

This beam pattern P is measured and recorded as a two-dimensional or three-dimensional map using the source 14 and the detector 16. In FIG. 3, the detector 16 is of a known type of linear detector comprising a plurality of side-by-side detector elements 34. This type of detector 16 is inherently capable of producing separate signals representative of the radiation flux intensity received by each detector element 34. Because the element-to-element spacing is known, the linear detector 16 can generate a one-dimensional map of the flux pattern P. To begin the mapping process, the linear detector 16 is oriented parallel to a lateral or "Y" axis and positioned at a specific first distance along the longitudinal or X-axis from the source 14. This positioning may be accomplished by a combination of movement of the source 14 and/or the detector 16. Appropriate means such as position transducers (not shown) are provided so that the position of each of the manipulators 22, 24, and 30 can be displayed and/or recorded. This information, in combination with the known dimensions of the source 14, detector 16, shield 28, and manipulators 22, 24, and 30 can be used to derive the position of the source 14, detector 16, and shield 28 with respect to a coordinate origin "O" (see FIG. 1). In some instances, the absorption characteristics of the target 12 may have a significant effect on the image quality. Accordingly, the target 12 (not shown in FIG. 3) may be placed between the source 14 and the detector 16, in approximate alignment, during the mapping process.

Once the initial position is set, the radiation source 14 is then activated, and the radiation flux striking each detector element 34 is recorded, for example in an electronic file record in the controller 26, or it may be displayed on a display 36 (see FIG. 1) for viewing by a user. This in effect produces a one-dimensional representation of the beam pattern P, and the flux distribution therein, in the Y-direction. The detector 16 is then moved to another position along the X-axis, and the radiation flux striking each detector element 34 is again recorded or displayed. These steps are repeated until a group of records defining a two-dimensional map of the beam pattern P is completed. If an area detector (not shown) is used, then the record at each X-axis position will be a two-dimensional representation, and the complete map will be a three-dimensional model of the beam pattern P.

When this map is completed, there will typically be one or more identifiable regions of special interest in the beam pattern P. One region typically has the most uniform flux level. This is represented schematically by the boundary labeled "U" in FIG. 3. There is also another region having the highest flux level, typically the center region of the beam pattern P, represented schematically by the boundary labeled "H" in FIG. 3. When the complete map has been stored, these regions of interest can be identified by their coordinates.

Optionally, the inspection system 10 may include one or more auxiliary detectors 29. These are relatively inexpensive, low-resolution digital detectors of a known type, for example of the type and size used for dental bite-wing images. One are more of these auxiliary detectors 29 are mounted around the perimeter of the shield 28, for example at each corner and/or at mid-span locations around the edges, and connected to the controller 26 as shown in FIG. 1. If the alignment or collimation is not working as planned, for example if one of the manipulators makes an errant move, it will result in a detectable flux at one of the auxiliary detectors 29. A similar set of auxiliary detectors 29' may be used with the inspection system 10' shown in FIG. 2.

The inspection system 10 may be programmed to automatically shut down the source 14 if a flux beyond a predetermined threshold level is observed by any of the auxiliary detectors 29. The pattern of response, i.e. the difference in signals from the individual auxiliary detectors 29 may also be used to determine how the source 14, detector 16, and/or shield 28 should be moved to correct the alignment problem.

Figure 4:
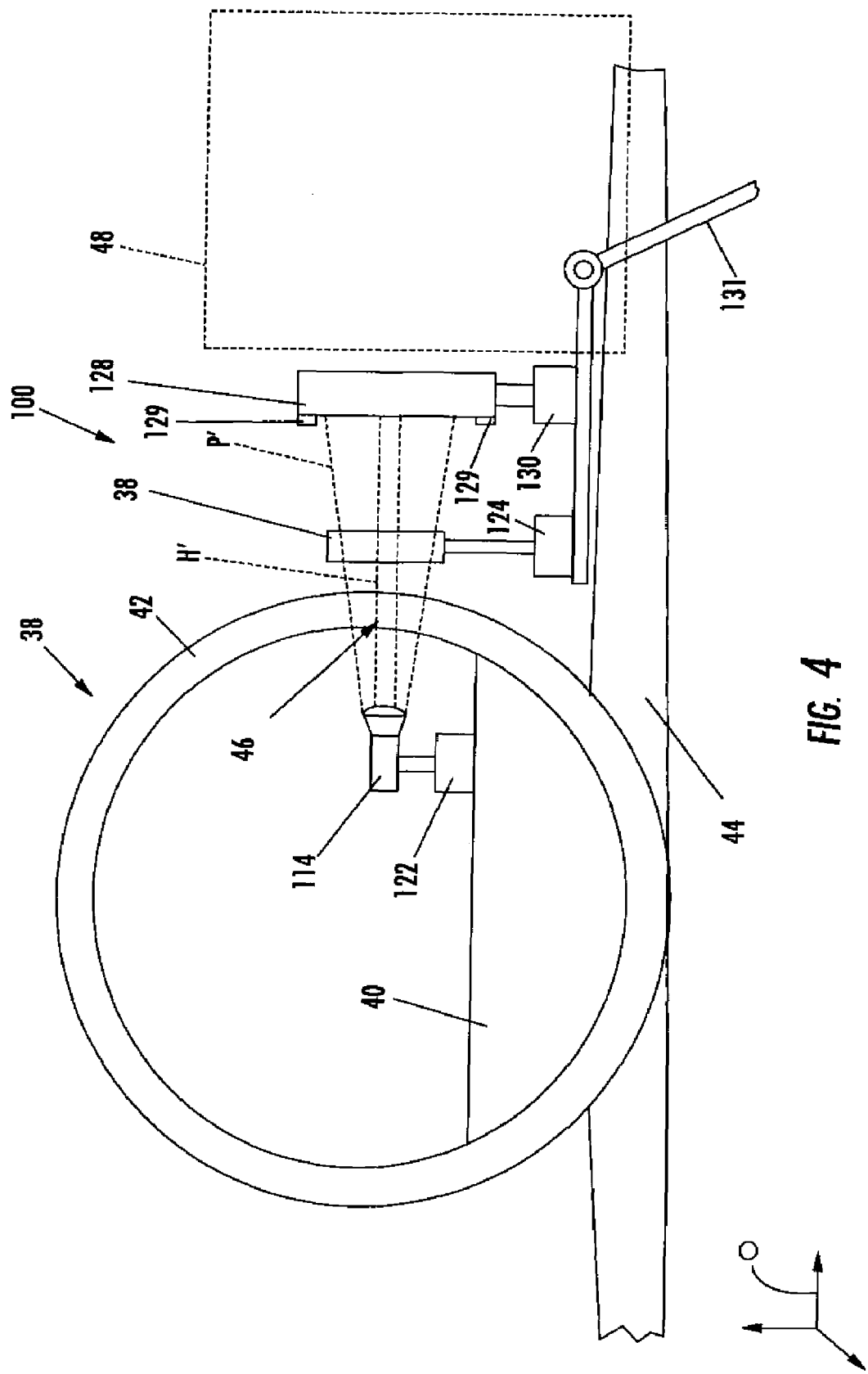
FIG. 4 is a schematic view of a radiographic inspection system in place next to an aircraft fuselage.

After the map is stored, this information can then be used to align the source 14, detector 16, and shield 28 as necessary for an inspection or measurement process. An example of this is shown in FIG. 4, which depicts an inspection apparatus 100 including a source 114 disposed inside an aircraft fuselage 38 having a deck 40, an outer wall 42, and a wing 44. The source 114 is mounted to the deck 40 by a first manipulator 122. A detector 116 is positioned outside the fuselage 38 by a second manipulator 124, and a shield 128 is positioned outside the fuselage 38 by a third manipulator 130. The second and third manipulators 124 and 130 may be carried by an articulated boom 131 supported by a truck or other ground vehicle of a known type (not shown). It is also possible that the source 114, detector 116, and shield 128 could all be carried by the boom 131 without using separate manipulators. With this arrangement, there is no line-of-sight between the source 114 and the detector 116, so manual alignment would require much trial and error. After the source 114, detector 116, and shield 128 are placed, they are aligned with reference to the previously-created map. In other words, the detector 116 is positioned at coordinates in space that will be within the beam pattern P' when the source 114 is activated. The first and second manipulators 122 and 124 are used to move the source 114 and/or detector 116 to achieve this alignment. In the illustrated example, a high-flux region "H'" is aligned with the approximate center of the detector 116. This is possible because the coordinates of the high-flux region H' within the beam pattern P are known relative to the coordinates of source 114 and/or the coordinate origin "O".

The present method can also be used to align the inspection apparatus 100 relative to the target, such as the fuselage wall 42. For example, the source 114, fuselage wall 42, and detector 116 may be relatively positioned so that the high-flux-intensity region H' passes through a predetermined area 46 of the fuselage wall 42.

The method of the present invention may also be used to align the shield 128. As shown in FIG. 4, the shield 128 is positioned by the manipulator 130 so that the boundaries of the beam pattern P' are within its vertical and horizontal extents at a selected distance from the source 114. The shield 128 absorbs the radiation from the source 114 so that a work area 48, that would ordinarily be a danger zone, is protected. Auxiliary detectors 129, similar to auxiliary detectors 29 described above, may be used with the inspection system 100, along with automatic shutdown and/or alignment correction features as noted above, if desired. Because the boundaries of the beam pattern P' are known, this work area 48 can be protected with greater certainty and with a smaller amount of shielding material than if manual alignment were used. Furthermore, the need for personnel for personnel to manually measure radiation around the inspection system 100 to establish effective shielding is eliminated.

The foregoing has described a method for aligning a radiographic inspection system. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation, the invention being defined by the claims.

What is claimed is:

1. A method for aligning a radiographic inspection system, comprising the steps of:
   providing a radiation source capable of emitting a beam pattern;
   positioning a detector to receive radiation emitted from the radiation source;
   causing the radiation source to emit the beam pattern;
   determining the distribution of flux intensity of the beam pattern;
   relatively positioning the radiation source and the detector with reference to the distribution of flux intensity, so that the detector is disposed at a predetermined location within the beam pattern;
   providing a shield for absorbing radiation; and
   relatively positioning said radiation source and said shield with reference to said distribution of flux intensity, so that said shield is at a predetermined position relative to said beam pattern.

2. The method of claim 1 further comprising creating a human-readable visual representation of said beam pattern.

3. The method of claim 1 further comprising creating a computer-readable representation of said beam pattern.

4. The method of claim 1 further comprising storing an electronic record of said distribution of flux intensity.

5. The method of claim 1 wherein said shield is supported by a manipulator operable to move said shield in response to a command.

6. The method of claim 1 wherein said shield is mounted in a fixed position relative to said detector.

7. The method of claim 1 further comprising:
   providing at least one auxiliary detector, said auxiliary detector carried by said shield in a location such that radiation flux from said radiation source will be received by said auxiliary detector when said detector is not disposed in said predetermined position within said beam pattern.

8. The method of claim 7 further comprising stopping said radiation source from emitting said beam pattern when a radiation flux exceeding a predetermined level strikes said auxiliary detector.

9. The method of claim 7 further comprising:
   providing a plurality of auxiliary detectors carried at spaced-apart locations by said shield; and
   receiving radiation from said radiation source by at least one of said auxiliary detectors; and
   generating an error signal based on the difference between the radiation flux received at each of said auxiliary detectors.

10. The method of claim 1 further comprising:
    providing a target to be inspected; and
    relatively positioning said radiation source and said target with reference to said distribution of flux intensity, so that said target is at a predetermined position relative to said beam pattern.

11. A method for aligning a radiographic inspection system, comprising the steps of:
    providing a radiation source capable of emitting a beam pattern;
    positioning a detector at a first position relative to the radiation source, so as to receive radiation emitted from the radiation source;
    causing the radiation source to emit the beam pattern;
    creating a first group of records of the flux intensity received by the detector at a plurality of points on the detector;
    creating a map comprising the records, the map describing the flux intensity at a plurality of positions within the beam pattern;
    relatively positioning the radiation source and the detector with reference to the map, so that the detector is disposed at a predetermined location within the beam pattern;
    providing a shield for absorbing radiation; and
    relatively positioning said radiation source and said shield with reference to said map, so that said shield is at a predetermined position relative to said beam pattern.

12. The method of claim 11 wherein said predetermined location is an area of the highest average flux intensity within said beam pattern.

13. The method of claim 11 wherein said predetermined location is a region of the most uniform flux intensity within said beam pattern.

14. The method of claim 11 wherein said detector is a linear detector comprising:
    a plurality of side-by-side detector elements; and
    means for generating a signal representative of the flux intensity received by each of said detector elements.

15. The method of claim 11 wherein said detector is an area detector comprising:
    a two-dimensional array of detector elements; and
    means for generating a signal representative of the flux intensity received by each of said detector elements.

16. The method of claim 11 wherein said shield is supported by a manipulator operable to move said shield in response to a command.

17. The method of claim 11 wherein said shield is mounted in a fixed position relative to said detector.

18. The method of claim 11 further comprising:
    providing at least one auxiliary detector, said auxiliary detector carried by said shield in a location such that radiation flux from said radiation source will be received by said auxiliary detector when said detector is not disposed in said predetermined position within said beam pattern.

19. The method of claim 11 further comprising stopping said radiation source from emitting said beam pattern when a radiation flux exceeding a predetermined level strikes said auxiliary detector.

20. The method of claim 11 further comprising:
    providing a plurality of auxiliary detectors carried at spaced-apart locations by said shield; and
    receiving radiation from said radiation source by at least one of said auxiliary detectors; and
    generating an error signal based on the difference between the radiation flux received at each of said auxiliary detectors.

21. The method of claim 11 further comprising:
    providing a target to be inspected; and
    relatively positioning said radiation source and said target with reference to said map, so that said target is at a predetermined position relative to said beam pattern.

* * * * *

UNITED STATES PATENT AND TRADEMARK OFFICE
CERTIFICATE OF CORRECTION

PATENT NO.         : 7,341,376 B2
APPLICATION NO. : 11/277269
DATED                : March 11, 2008
INVENTOR(S)      : Birdwell It is certified that error appears in the above-identified patent and that said Letters Patent is hereby corrected as shown below:

Col 2 under "DETAILED DESCRIPTION OF THE INVENTION"

-Column 2, line 39, delete "in come cases" and enter --in some cases--.

-Column 3, line 61, delete "One are more of these" and enter --One or more of these--.

-Column 4, line 58, delete the duplicate wording of "for personnel".

Signed and Sealed this

Twenty-second Day of July, 2008

JON W. DUDAS
*Director of the United States Patent and Trademark Office*